(12) United States Patent
Sager

(10) Patent No.: US 7,445,449 B2
(45) Date of Patent: Nov. 4, 2008

(54) CONTINUOUS PRODUCTION CROWN CORE/CROWN MAKING PROCESS

(76) Inventor: Robert David Sager, 1919 Poyntz Ave., Manhattan, KS (US) 66502

( * ) Notice: Subject to any disclaimer, the term of this patent is extended or adjusted under 35 U.S.C. 154(b) by 41 days.

(21) Appl. No.: 11/023,950

(22) Filed: Dec. 28, 2004

(65) Prior Publication Data

US 2006/0115794 A1 Jun. 1, 2006

Related U.S. Application Data

(60) Provisional application No. 60/631,102, filed on Nov. 26, 2004, provisional application No. 60/566,855, filed on Apr. 30, 2004, provisional application No. 60/543,038, filed on Feb. 6, 2004.

(51) Int. Cl.
*A61C 8/00* (2006.01)
(52) U.S. Cl. .................. 433/223; 29/896.1; 72/338
(58) Field of Classification Search ................ 433/223, 433/202.1; 72/338, 339; 29/896.1
See application file for complete search history.

(56) References Cited

U.S. PATENT DOCUMENTS

| 4,439,154 | A | * | 3/1984 | Mayclin ...................... 433/229 |
| 4,615,678 | A | * | 10/1986 | Moermann et al. ........ 433/201.1 |
| 4,826,430 | A | * | 5/1989 | Chen et al. ...................... 433/8 |
| 5,092,022 | A | * | 3/1992 | Duret ........................ 29/896.1 |
| 5,135,393 | A | * | 8/1992 | Eidenbenz et al. ............ 433/53 |
| 5,266,878 | A | * | 11/1993 | Makino et al. ............... 318/571 |
| 5,322,436 | A | * | 6/1994 | Horng et al. ................... 433/23 |
| 5,933,353 | A | * | 8/1999 | Abriam et al. ............... 700/182 |
| 6,345,984 | B2 | * | 2/2002 | Karmaker et al. ........... 433/173 |
| 6,406,295 | B1 | * | 6/2002 | Mahler ........................ 433/173 |
| 6,454,568 | B1 | * | 9/2002 | Beuschel et al. ............. 433/163 |
| 6,780,012 | B1 | * | 8/2004 | Peterson ....................... 433/90 |
| 6,790,040 | B2 | * | 9/2004 | Amber et al. ................ 433/173 |
| 6,886,462 | B2 | * | 5/2005 | Dick et al. ................... 101/483 |
| 6,979,496 | B2 | * | 12/2005 | Haymann et al. ......... 428/542.8 |
| 7,178,731 | B2 | * | 2/2007 | Basler .................... 235/462.01 |

(Continued)

FOREIGN PATENT DOCUMENTS

| JP | 63005730 | * | 1/1988 |
| JP | 07008506 | * | 1/1995 |

*Primary Examiner*—Ralph A Lewis
(74) *Attorney, Agent, or Firm*—Sonnenschein Nath & Rosenthal LLP; Bryan P. Stanley

(57) ABSTRACT

A system for continuous production of prosthodontic pieces such as crown cores, crowns or the like is provided. The system utilizes turning and milling on a live center CNC machine of a rod stock of material for making the pieces such as Bio-HIP Y-TZP (High Heat and Isostatic Pressure formed ytrium stabilized zirconium dioxide) that is automatically feed into the machine. Multiple pieces are cut one after another from the continuous rod stock. The machine includes a an engraving unit that marks pieces after they are cut with an identification mark such as a certification mark and/or an identification code. In one embodiment, multiple machines are utilized in which each machine is fed a rod stock of a different shape and/or size. A central control unit obtains Cad/Cam specifications for a piece that is to be cut and selects the machine on which the piece is to be made by determining the rod stock that will require the least amount of cutting.

11 Claims, 4 Drawing Sheets

U.S. PATENT DOCUMENTS

| | | | |
|---|---|---|---|
| 2002/0076530 A1* | 6/2002 | MacDougald et al. | 428/195 |
| 2002/0137002 A1* | 9/2002 | Bodenmiller | 433/51 |
| 2003/0132539 A1* | 7/2003 | Althoff et al. | 264/16 |
| 2004/0241614 A1* | 12/2004 | Goldberg et al. | 433/202.1 |
| 2005/0276672 A1* | 12/2005 | Prince et al. | 409/234 |
| 2006/0111806 A1* | 5/2006 | Kraemer et al. | 700/117 |

* cited by examiner

US 7,445,449 B2

CONTINUOUS PRODUCTION CROWN CORE/CROWN MAKING PROCESS

This application claims priority pursuant to 35 U.S.C. 119(e) to U.S. Provisional Patent Application Ser. No. 60/631,102, filed Nov. 26, 2004, U.S. Provisional Patent Application Ser. No. 60/566,855, filed Apr. 30, 2004 and U.S. Provisional Patent Application Ser. No. 60/543,038, filed Feb. 6, 2004, the entire disclosures of which are incorporated herein by reference.

FIELD OF THE INVENTION

The present invention relates generally to prosthodontic systems, methods and apparatuses. More particularly, the present invention is concerned with a process for manufacturing custom dental crown and bridge cores and/or crowns and bridges, which provides economy of manpower, time, materials and machine.

BACKGROUND OF THE INVENTION

Prior to the advent of the instant invention, prosthodontic systems have been extremely labor intensive and time consuming, requiring a considerable amount of skilled labor to custom hand-make each prosthodontic unit for each case. Recent prior art CAD/CAM-CNC systems for manufacturing prosthodontic pieces require new skill sets and higher intellectual levels of skill than older systems, forcing the majority of labs in the USA (1-5 person small labs) to resist adopting advanced materials and methodologies and/or have to outsource such capabilities and subsequently label the result "premium" goods and services. Even through outsourcing, contemporary technological prior art prosthodontic systems are extremely inefficient, making the availability of high quality, cost-effective prosthodontic pieces nonexistent.

Examples of a prior art prosthodontic systems include the Lava™ two-stage zirconium dioxide system offered by 3M ESPE, and the Precident™ one-stage Bio-HIP Y-TZP (High Heat and Isostatic Pressure formed ytrium stabilized tetragonal zirconium polymorph) offered by DCS of Switzerland. The Lava™ System utilizes a zirconia dioxide block that is CNC milled in a greenware state then secondarily heat sintered. The Precident System mills directly from the harder presintered Bio-HIP Y-TZP block.

My prior inventions disclosed in U.S. patent application Ser. Nos. 60/566,855, filed Apr. 30, 2004 and 60/543,038 filed Feb. 6, 2004, the disclosures of which are incorporated herein by reference in their entirety, provide systems for simultaneously manufacturing a custom dental crown coping and ceramic infrastructure (abutment or ceramic portion of the abutment if two piece) to reduce the amount of labor, time and materials. My prior inventions can be used to manufacture pieces from a greenware stage prior to sintering, or alternatively from an already ceramic infiltrated sintered material, such as a Bio-HIP Y-TZP. Notwithstanding, all prior art processes discussed above mill crown and bridge cores/crowns and bridges from a single block of material with a single axis machine. All current systems require that a technician continuously attend the CNC crown and bridge core/crown and bridge machines to load and change blocks after a limited number of units are produced, and to manually separate finished units from the blocks to avoid trial and error "fit" re-identification.

The maximum number of crown core/crown pieces that any system of the prior art can currently make is 8-16 units/day (capable with a DCS machine, which can cut from 2 blocks before requiring shut down and material exchange), which can take in excess of 24 hours and which requires individual separation of the units from blocks by hand. All other machines (other than a DCS machine) require the block/lug to be changed for each crown/crown core, or at least one block change for each 3-4 crown or bridge core/crown and bridge units. For example, Hint-ELs® Zirconium TZP HIP, which comes in a disc (similar to a hockey-puck) shape for cutting bridges and a two-stage cylindrical (similar to a magic marker) shape for individual pieces, can be automatically feed into a milling machine such that multiple pieces can be cut without the requirement that an attendant mechanically remove the completed work and que-up materials from a hopper on the machine. Nevertheless, as each piece is unique, such machines must be shut down for removal of the pieces after they are cut to avoid confusion among multiple pieces. All machines, other than a DCS machine, cut crown core/crowns from a non-sintered greenware stage. In such machines, the exchange of blocks is manual, and time consuming. Although the process is "computer numeric controlled" (CNC—meaning that a human does not have to manually make the piece), the production time and set up is such that the technician has to continuously monitor the machinery or at the least be mindful of the ticking clock and the end of the process. Thus, true automation efficiencies in the work place are difficult, if not impossible to obtain.

All prior art processes recognize the TZP phase of zirconium to be the strongest of the metal-free materials. Unfortunately, all metals have trace elements that may irritate some individuals' soft tissues. Bio-HIP Y-TZP provides a non-metal hypo-allergenic option for manufacturing crown and bridge cores/crowns and bridges; however Bio-HIP Y-TZP is expensive, hard to work with, and so hard it eats diamond burs in the manufacturing process. Therefore, none of the processes of the prior art (whether cutting either non-sintered or sintered material) are efficient enough to make safe non-metal crown cores readily available and/or affordable for all people, and are intended primarily at present for affluent patients.

Using Bio-HIP Y-TZP via CAD/CAM and CNC manufacturing is known to offer the most precision as no variable result post production process is required (i.e. sintering). Notwithstanding, the prior art systems waste too much material (raw material and burs) and take too long, making what is the best material for crown core/crowns expensive. Thus, the use of Bio-HIP Y-TZP through prior art processes is not cost effective enough in production to make the best product available for all patients. Therefore, it would be beneficial to provide a process that increases the efficiency of using materials such as Bio-HIP Y-TZP for individual crown cores/crowns so as to eliminate socio-economic discrimination in dentistry, and level the playing field in price and honesty of materials used.

SUMMARY OF THE INVENTION

An object of the instant invention is to provide a system for manufacturing prosthodontic pieces such as individual crown cores, crowns, or the like. Another object of the instant invention is to provide a system for utilizing materials such as Bio-HIP Y-TZP for manufacturing prosthodontic pieces such as individual crown cores, crowns, or the like that is cost effective. Another object of the instant invention is to truly "automate" the crown core/crown making process, such that it can be largely unattended after CAD/CAM instructions are given to the CNC machinery. Yet another object of the instant invention is to provide a method of certifying and identifying custom pieces made by the automated process of the instant invention. Still another object of the instant invention is to provide a continuous production crown core/crown making process that utilizes turning and multiple axis milling on a live center CNC machine.

The objects of the instant invention are accomplished through the use of a continuous feed live center CNC machine for crown core/crown manufacture and Bio-HIP Y-TZP rods stock that is fed into the CNC machine. The rod stock of the instant invention may be formed in any and all cross sectional shapes (i.e., hex, round, triangular, square, Christmas tree, etc.), and preferably is available in a plurality of shapes and sizes to be used in the continuous feed crown core/crown machines for manufacturing pieces of varying shapes and sizes. The particular cross sectional shape and/or size utilized for a particular piece will be programmed to be selected by the machine so as to minimize the amount of cutting and waste of material, and to expedite the manufacturing process.

The process of the instant invention utilizes specialized software, whether from prior art or by the instant invention, to interface between CAD/CAM design programs and CNC machines to enable the machine to use multiple cutting tools at one time simultaneously and/or individually and sequentially to continuously produce crown cores/crowns. In a preferred embodiment, the software is used by a central control unit that is connected to and controls a plurality of cutting machines.

The CNC machine of the instant invention also includes a high energy (i.e. laser, etc.) or mechanical engraving tool to provide an identity marking code on each crown core/crown manufactured by the process of the instant invention at the end of production. The marking on each piece is able to be subsequently scanned for sorting and positive identification and certification of process used. The identification mark on each piece can be scanned by an electronic scanning device, such as a bar code scanner, and pieces can then be rapidly hand sorted or automatically sorted by machinery connected to the scanning device. It is noted because the individual crown cores are manufactured and totally separated from a rod, with the final cut off occurring at a single point on the external occlusal/incisal surface, minimal hand finishing will be required, and the identity marking code may then be placed anywhere on the external surface. Such opportunity is not possible on any other prior art, requiring subsequent finishing and/or material altering processes.

The instant invention truly "automates" the crown core/crown making process, such that it can be largely unattended after CAD/CAM instructions are given to the machinery, and that the core requires the minimum of manual finishing and handling during and after manufacture. The rod stock is loaded into the machine, and the machine requires no further user interaction until the rod stock is used up. In a preferred embodiment of the instant invention multiple CNC machines are loaded with multiple rods (of varying shapes and sizes) and multiple cutting tools. Much in the same way Henry Ford's assembly line automated the automobile industry, the instant invention allows the CNC process of the instant invention to be operated in a highly automated "factory" style, rather than primarily custom "small shop" style.

In a preferred embodiment of the instant invention, dentists (or their labs) may only own scanners, and transmit via modem (or an other data transmission device) the digital information obtained by the scanner to a central factory, or to one of multiple centers able to make the crown coping. Then the dentist and/or lab need only a finish porcelain technician, instead of the entire staff of technicians required to make the crown cores. Although similar "outsourcing" may be feasible for the manufacture of crown cores through prior art processes, the time and cost of Bio-HIP Y-TZP make the use of Bio-HIP Y-TZP zirconium a premium rather than a standard offering.

The high energy (i.e. laser, etc.) or mechanical engraver of the instant invention provides a method of certifying the origin and material, trademark (similar to the DeBeers marks for diamonds) of pieces, as well as a method of identifying pieces for tracking and/or sorting, by marking each crown core/crown manufactured from the rod stock with a marking after it is cut. It is noted at present, there is no federal, state or local educational or licensure requirement for dental laboratory technicians, and no federal, state or local requirement for materials used in dental prostheses, such as crowns and bridges. By marking the units, the instant invention offers the first opportunity for certification of material, material lots and processes through to completed dental prostheses. Such markings are less feasible with prior art processes that require post production processes (i.e. sintering), as such processes would burn, melt or grind away the marking. Individual crowns manufactured by prior art processes in which a crown is cut from a single block, may also be marked through the instant invention. Nevertheless, marking pieces manufactured from rod stock of the instant invention provides a particular advantage that is unnecessary in non-automated processes, as the mass production of pieces through the instant invention presents the possibility of disorganization and confusion of finished pieces.

As is discussed above, multiple CNC machines of the instant invention may be loaded with differing diameters and/or shapes of rod stock. In a preferred embodiment of the instant invention, all of the machines are controlled by a central control unit so that the control unit can automatically put the crown core/crown into production on the machine loaded with the most appropriate size rod stock, and thereby conserve both raw material and bur stock, as well as reduce the time it takes to cut away material by minimizing the amount of material that needs to be cut away. The rod stock of the instant invention may be of a variety of lengths, preferably anywhere from 3 cm to 3 meters, to optimize the versatility to small and big shops and or supply of the rod stock. The automatic feed of the rod stock to the machine minimizes user interaction, only requiring the technician to be an attendant to monitor and periodically change and/or spot check calibration of tools of the many machines, rather than having to constantly feed the machines raw material blocks/purge from the machines of finished pieces and then restart manually them.

In the preferred embodiment of the instant invention, rod stocks are a Bio-HIP Y-TZP (High Heat and Isostatic Pressure formed ytrium stabilized tetragonal zirconium polymorph) material. Nevertheless, it will be appreciated that other suitable materials, such as titanium or modern synthetics, that do not require post production processes may be utilized to manufacture pieces without departing from the spirit and scope of the instant invention. It will further be appreciated that certain features of the instant invention may also be utilized with materials that require post production processes without departing from the spirit and scope of the instant invention.

The foregoing and other objects are intended to be illustrative of the invention and are not meant in a limiting sense. Many possible embodiments of the invention may be made and will be readily evident upon a study of the following specification and accompanying drawings comprising a part thereof. Various features and subcombinations of invention may be employed without reference to other features and subcombinations. Other objects and advantages of this invention will become apparent from the following description taken in connection with the accompanying drawings, wherein is set forth by way of illustration and example, an embodiment of this invention and various features thereof.

BRIEF DESCRIPTION OF THE DRAWINGS

A preferred embodiment of the invention, illustrative of the best mode in which the applicant has contemplated applying the principles, is set forth in the following description and is shown in the drawings and is particularly and distinctly pointed out and set forth in the appended claims.

DETAILED DESCRIPTION OF A PREFERRED EMBODIMENT

As required, a detailed embodiment of the present inventions is disclosed herein; however, it is to be understood that the disclosed embodiment is merely exemplary of the principles of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
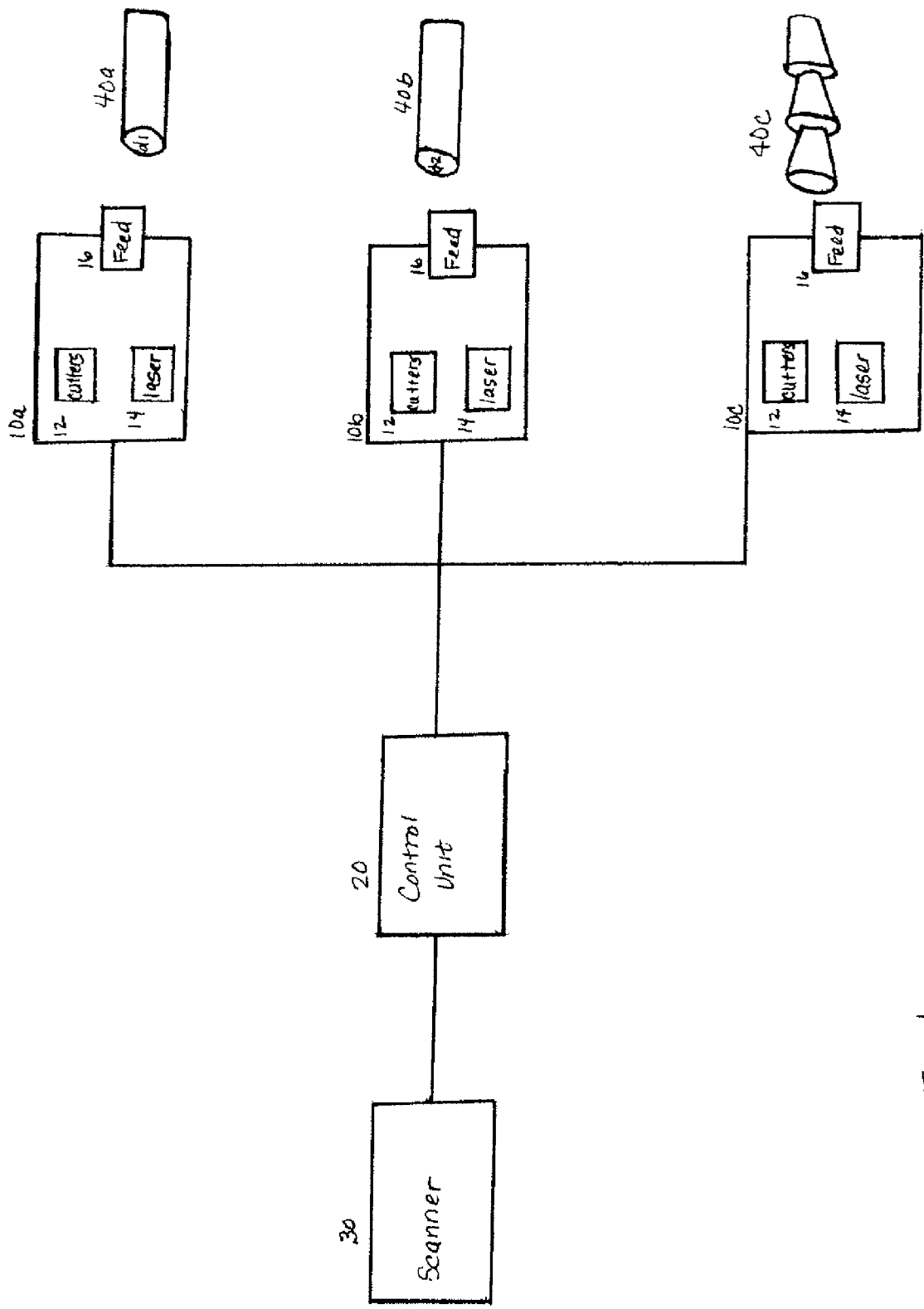
FIG. 1 is a schematic diagram of a preferred embodiment system for continuously making a plurality of prosthodontic pieces such as crowns, crown cores, or the like, of the instant invention.

Referring to FIG. 1 a preferred embodiment of a system of the instant invention is shown in which a plurality of cutting machines 10a, 10b and 10c are connected to central control unit 20. Control unit 20 is connected to scanner 30. Each of machines 10a, 10b and 10c include cutting tools 12, laser engraving units 14, and automatic rod stock feeders 16. Rod stocks of varying cross-sectional shapes and sizes are loaded into machines 10a, 10b and 10c. In the embodiment shown in FIG. 1 each of machines 10a, 10b and 10c is fed a rod stock having a different cross-sectional shape and/or size from the rod stocks in the other of machines 10a, 10b and 10c. For example, machine 10a utilizes rod stock 40a having a circular cross-sectional shape of a first diameter, $d_1$, for cutting larger pieces such as molars; machine 10b utilizes rod stock 40b having a circular cross-sectional shape of a second diameter, $d_2$, smaller than the first diameter, $d_1$, for cutting smaller pieces such as incisors; and machine 10c utilizes rod stock 40c having a Christmas-tree cross-sectional shape for cutting crowns.

In operation, control unit 20 receives specifications for a piece that is to be cut from scanner 30. Scanner 30 may be located in close proximity to control unit 20 and machines 10a, 10b and 10c. Alternatively, scanner 30 may be located remote from control unit 20, such as in a dental office or lab, and control unit 20 and machines 10a, 10b and 10c may be located in a central factory or manufacturing center. In the embodiment shown in FIG. 1, scanner 30 is a stand alone scanner already available in the art and may include appropriate CAD/CAM software for obtaining specifications for a piece that is to be cut (either internally to the scanner or in a computer to which the scanner is connected). In such an embodiment, the dental professional will use the scanner to obtain specifications for the piece that is to be manufactured and transmit the specifications electronically (such as via modem) to the central factory.

Figure 2A:
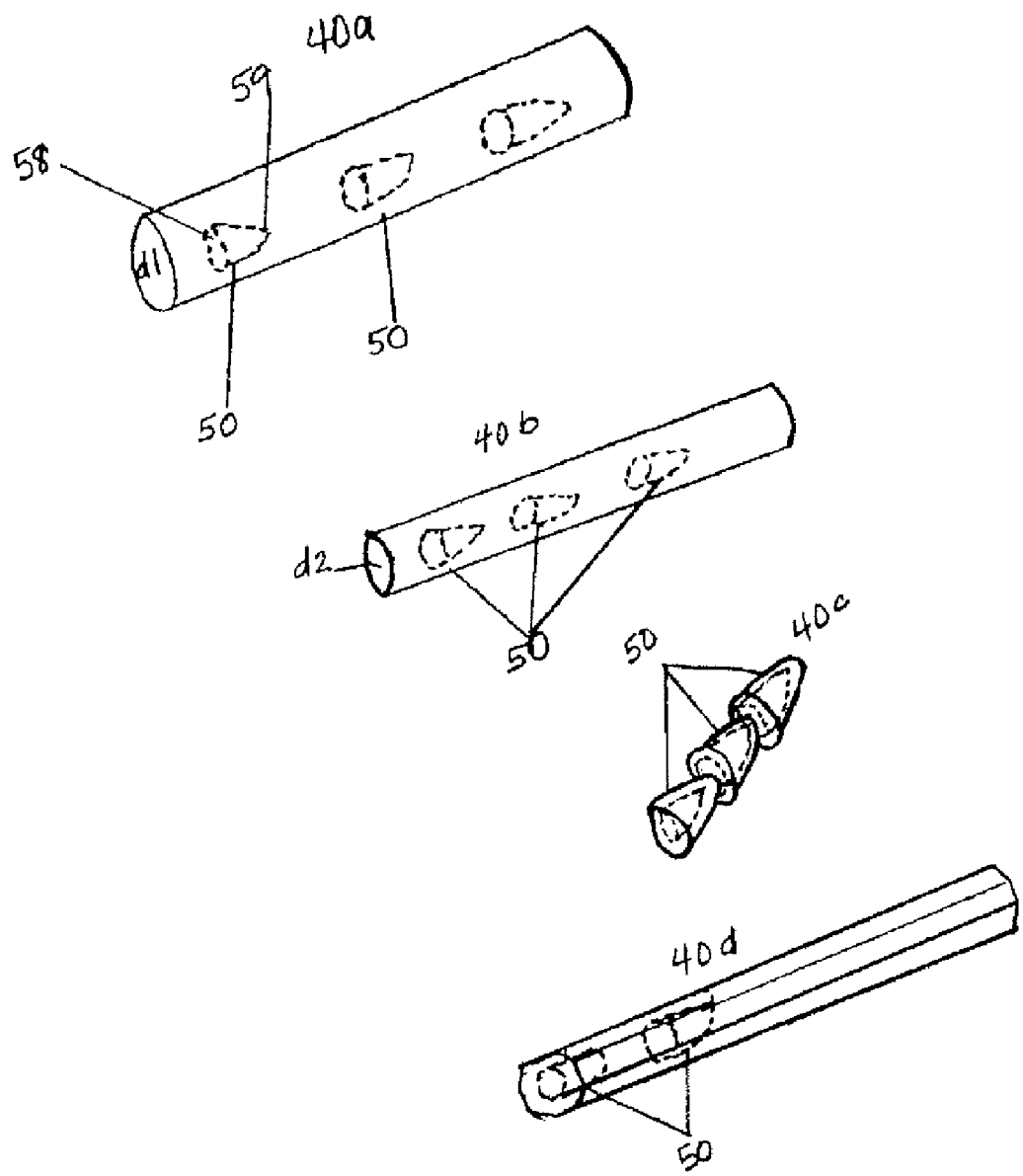
FIG. 2a is a perspective view of various rod stocks of the instant invention and prosthodontic pieces made in accordance with the instant invention.
Figure 2B:
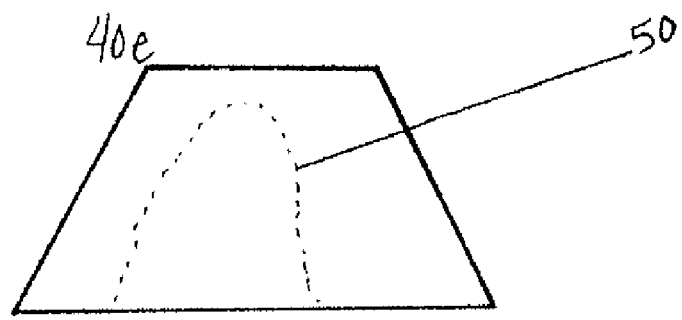
FIG. 2b is a sectional view of various rod stocks of the instant invention and prosthodontic pieces made in accordance with the instant invention.
Figure 2B:
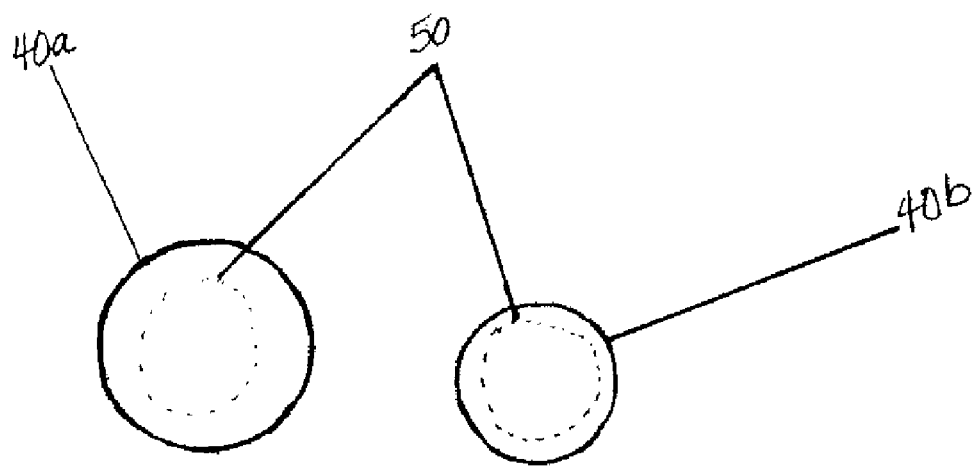

The use of different cross-sectional shapes and sizes in each of machines 10a, 10b and 10c allows a rod stock to be selected for cutting a particular piece 50 so as to minimize the amount of material that must be cut away from the rod stock to make the piece. This decreases cutting time, saves material and minimizes wear on the machine. Once controller 20 obtains specifications for piece 50 from scanner 30 control 20 will determine from the variety of rod stock available the shape and size most appropriate for piece 50. As is shown in FIGS. 2a and 2b, the rod stock (referred to generally as reference number 40) can available in a variety of different shapes and sizes to allow many different shapes and sizes of pieces to be cut while resulting in minimal waste of material and maximizing efficiency of the cutting process. Rod stock 40 shapes and sizes include, but are not limited to, circular cross-section rod stock 40a having diameter $d_1$ for cutting larger pieces such as molars; circular cross-section rod stock 40b having a smaller diameter $d_2$ for cutting smaller pieces such as incisors; Christmas tree rod stock 40c for cutting pieces such as crowns; hexagonal cross-section rod stock 40d; and quadrilateral cross-section rod stock 40e. Referring to FIG. 2b in particular, it can be seen that the circular rod stock 40b having diameter $d_2$ is a more appropriate cross sectional size for piece 50 than rod stock 40a having larger diameter $d_2$, as the larger cross section diameter of 40a results waste of material and requires considerably more cutting than rod stock 40b.

In most rod stock shapes and sizes, it is preferred that pieces be cut along the axis of the rod stock, such that bottom 58 and top 59 of each piece 50 are both located on the axis of the rod stock, as is shown in FIG. 2a. Nevertheless, it will be appreciated that pieces may also be cut in which that hollowed bottom 58 and top 59 are located off of the axis of the rod stock (i.e. the piece is cut generally perpendicular to the axis—see 40e of FIG. 2b).

Once the appropriate machine having the desired rod stock shape and size is selected, controller 20 will activate feed mechanism 16 on the appropriate machine to feed rod stock 40 into machine 10 for cutting by cutters 12 and marking by laser marking unit 14, both of which are controlled by controller 20. The automatic feed mechanism 16 of machine 10 can be made in any manner now know or hereafter discovered for automatically moving rods, tubes and the like in an axial direction.

In a preferred embodiment of the instant invention cutting machines 10a, 10b and 10c are live center CNC machines that each include two cutting tools 12. The live center and two cutting tools allow a plurality of individual prosthodontic pieces to be sequentially cut from a continuous rod stock along multiple axes as the rod stock is continuously fed into the cutting machine without any human operator assistance.

Figure 3:
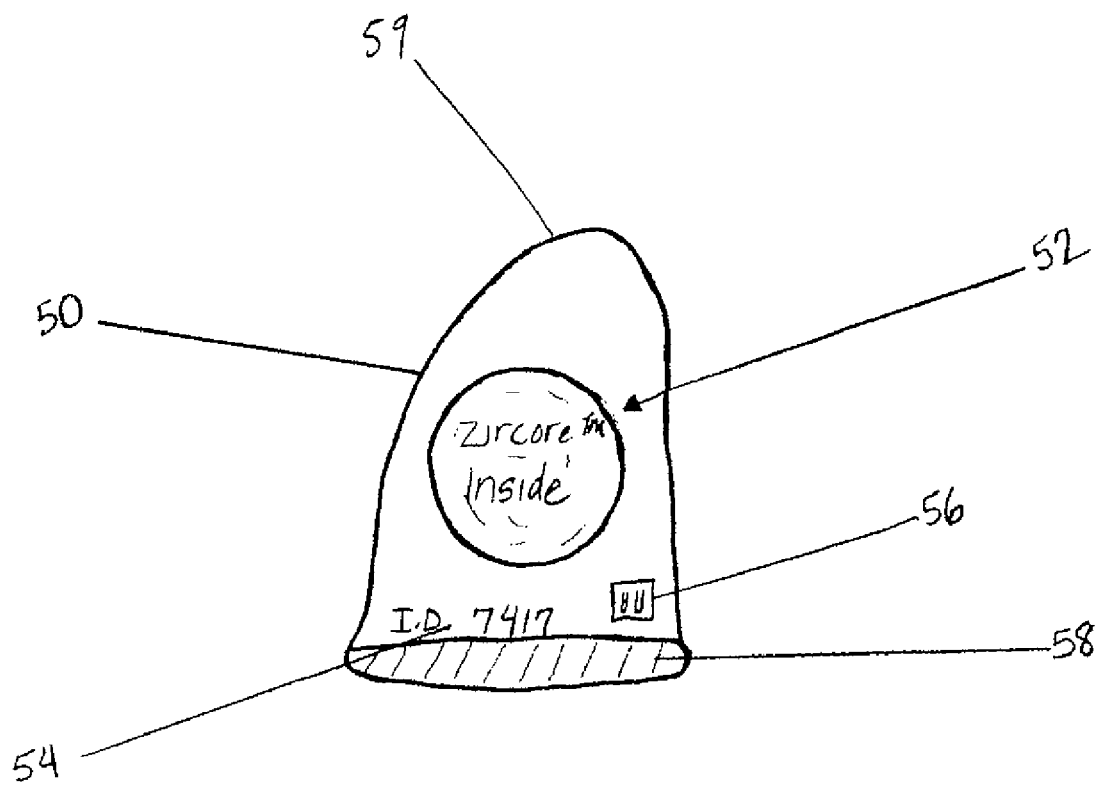
FIG. 3 is a front view of a prosthodontic piece made in accordance with the instant invention, including identification marks in accordance with several embodiments of the instant invention.

As the instant invention allows a plurality of pieces to be cut from a single continuous rod stock without operator interaction to replace the material for each new piece, confusion between pieces may occur. Therefore, machines 10a, 10b and 10c of the instant invention include laser marking units 14 to provide an identification mark on each piece after it is cut. As is shown in FIG. 3, the identification mark on piece 50 may include a certification mark 52 identifying the source and signifying the quality of piece 50, as well as a unique identification code for tracking and identifying the specific piece 50 which is most likely a customized prosthodontic piece. The unique identifying code of the instant invention may include piece identification number 54 and/or bar code 56, or any other identification code now known or hereafter discovered. It will be appreciated that although the marking unit of the preferred embodiment discussed herein is a laser-engraving unit, other marking units such as ink jets, etching, manual/mechanical engraving, etc., may be utilized without departing from the spirit and scope of the instant invention.

It will be appreciated that although the marking of prosthodontic pieces such as crowns, crown cores, or the like, made in accordance with the instant invention is sometimes referred to herein as being accomplished "after" the piece is cut, the actual marking can take place. as part of the cutting process. In such instance, the marking of the piece is referred to as being accomplished "after" the cutting of the piece as the marking is initiated "after" the cutting has been initiated. Accordingly, the completion of the cutting may precede, coincide with or even succeed completion of the marking without departing from the spirit and scope of the instant invention.

In the foregoing description, certain terms have been used for brevity, clearness and understanding; but no unnecessary limitations are to be implied therefrom beyond the requirements of the prior art, because such terms are used for descriptive purposes and are intended to be broadly construed. Moreover, the description and illustration of the inventions is by way of example, and the scope of the inventions is not limited to the exact details shown or described.

Although the foregoing detailed description of the present invention has been described by reference to an exemplary embodiment, and the best mode contemplated for carrying out the present invention has been shown and described, it will be understood that certain changes, modification or variations may be made in embodying the above invention, and in the construction thereof, other than those specifically set forth herein, may be achieved by those skilled in the art without departing from the spirit and scope of the invention, and that such changes, modification or variations are to be considered as being within the overall scope of the present invention. Therefore, it is contemplated to cover the present invention and any and all changes, modifications, variations, or equivalents that fall with in the true spirit and scope of the underlying principles disclosed and claimed herein. Consequently, the scope of the present invention is intended to be limited only by the attached claims, all matter contained in the above description and shown in the accompanying drawings shall be interpreted as illustrative and not in a limiting sense.

Having now described the features, discoveries and principles of the invention, the manner in which the invention is constructed and used, the characteristics of the construction, and advantageous, new and useful results obtained; the new and useful structures, devices, elements, arrangements, parts and combinations, are set forth in the appended claims.

It is also to be understood that the following claims are intended to cover all of the generic and specific features of the invention herein described, and all statements of the scope of the invention which, as a matter of language, might be said to fall therebetween.

What is claimed is:

1. A method of continuously making a plurality of prosthodontic pieces sized for positioning within a patient's mouth, said method comprising the steps of:
    feeding a rod of stock material into a cutting and shaping machine;
    operating said machine to cut individual pieces from said rod of stock material as the rod of stock material is fed into the machine and operating said machine to shape said cut individual pieces into a plurality of individual prosthodontic pieces;
    operating said machine to place a unique identification mark on each prosthodontic piece; and
    using said identification mark to avoid confusion between the plurality of individual prosthodontic pieces continuously produced by said machine.

2. The method as claimed in claim 1 wherein the step of using the identification mark to avoid confusion between the plurality of individual prosthodontic pieces further comprising the step of collecting the plurality of individual pieces for subsequent rapid sorting by identification mark.

3. The method as claimed in claim 1 wherein the unique identification mark comprises a unique identification code for each individual piece.

4. The method as claimed in claim 1 wherein the identification mark comprises a certification mark.

5. The method as claimed in claim 1 wherein the identification mark is made by a high energy source.

6. The method as claimed in claim 5, wherein the high energy source is a laser or mechanical engraving device.

7. The method as claimed in claim 1 wherein the step of operating said machine to cut individual pieces from said rod of stock material as the rod of stock material is fed into the machine and operating said machine to shape said cut individual pieces includes the step of removing material from the rod stock to form shapes of the individual prosthodontic pieces.

8. The method as claimed in claim 1 wherein the step of operating said machine to cut individual pieces from said rod of stock material as the rod of stock material is fed into the machine and operating said machine to shape said cut individual pieces includes the steps of turning and multiple axis milling on a live center CNC machine.

9. The method as claimed in claim 1 wherein the step of operating said machine to cut individual pieces from said rod of stock material as the rod of stock material is fed into the machine and operating said machine to shape said cut individual pieces includes the step of performing a final cut off for an individual prosthodontic piece on an external occlusal/incisal surface of the piece.

10. The method as claimed in claim 1 wherein the step of operating said machine to cut individual pieces from said rod of stock material as the rod of stock material is fed into the machine and operating said machine to shape said cut individual pieces includes the step of cutting individual prosthodontic pieces along multiple axes.

11. The method as claimed in claim 10 wherein the step of operating said machine to cut individual pieces from said rod of stock material as the rod of stock material is fed into the machine and operating said machine to shape said cut individual pieces is performed by at least two cutting tools.

* * * * *